United States Patent [19]

Bugaut et al.

[11] 4,419,101
[45] Dec. 6, 1983

[54] CHLORINE-SUBSTITUTED NITRO-PARA-PHENYLENEDIAMINES, A PROCESS FOR THEIR PREPARATION AND THEIR USE IN DYEING KERATIN FIBRES

[75] Inventors: Andree Bugaut, Boulogne-Billancourt; Jean Cotteret, Franconville, both of France

[73] Assignee: L'Oreal, Paris, France

[21] Appl. No.: 381,636

[22] Filed: May 24, 1982

[30] Foreign Application Priority Data

May 25, 1981 [FR] France ................. 81 10374

[51] Int. Cl.³ .................. A61K 7/13; C07C 87/60
[52] U.S. Cl. ........................... 8/415; 8/407; 564/441; 564/367; 564/369
[58] Field of Search ............. 8/415, 407; 564/441, 564/367, 369

[56] References Cited

FOREIGN PATENT DOCUMENTS 1127080 9/1968 United Kingdom .
1262752 2/1972 United Kingdom .

*Primary Examiner*—Natalie Trousof
*Assistant Examiner*—Vera C. Clarke
*Attorney, Agent, or Firm*—Fleit, Jacobson, Cohn & Price

[57] ABSTRACT

The invention provides new chlorine-substituted nitro-para-phenylenediamines of the formula:

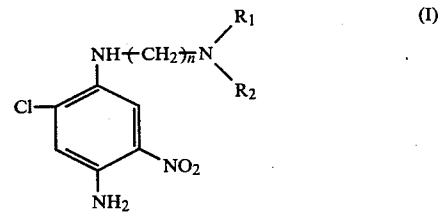

in which $R_1$ and $R_2$, which are identical or different, denote hydrogen, a lower alkyl group or a monohydroxylated or polyhydroxylated alkyl group and n is an integer from 2 to 4, and the cosmetically acceptable salts of these compounds. These compounds can be used for hair dyeing.

20 Claims, No Drawings

CHLORINE-SUBSTITUTED NITRO-PARA-PHENYLENEDIAMINES, A PROCESS FOR THEIR PREPARATION AND THEIR USE IN DYEING KERATIN FIBRES

The present invention relates to nitro-para-phenylenediamine derivatives, to their use in dyeing keratin fibres, and in particular human hair, and to a process for their preparation.

As is well known, it is common practice to provide the hair with a direct coloration, or a complementary sheen in the case of oxidation dyeing, using nitro derivatives of the benzene series. It has already been recommended to use nitro-para-phenylenediamines, such as nitro-para-phenylenediamine itself, both in direct dyeing and in oxidation dyeing.

However, the perfect harmlessness of nitro-para-phenylenediamine has been questioned in recent years, and attempts have therefore been made to replace this dyestuff in hair-dyeing compositions. Nitro-para-phenylenediamine is frequently used in hair dyeing in the formulation of warm shades, such as mahogany, or coppery chestnut containing a greater or less proportion of red, so that it is essential, for such formulations, to find other direct dyestuffs which make it possible to provide the keratin fibres with red shades. We have discovered nitro-para-phenylenediamines which are capable of providing red in hair-dyeing formulations.

It has also been found that the hair dyes obtained with the aid of this new class of dyestuffs have good stability to light and washing.

In addition to their noteworthy dyeing properties, the dyestuffs of the present invention have a good degree of harmlessness. In particular, these compounds have the advantage of being non-mutagenic. As is well known, the non-mutagenic character of dyestuffs is currently assessed with the aid of the Ames' test on *Salmonella typhimurium*. Tests carried out on the strains TA 1535, TA 1537, TA 1538, TA 98 and TA 100, with or without S₉ mix activated by Arochlor 1254, have made it possible to establish this fact.

These dyestuffs can also be used in oxidation dyeing compositions for obtaining, with the oxidation dyestuffs, shades having a rich sheen.

The present invention provides the nitro-para-phenylenediamines defined below, as well as dyeing compositions containing these nitro-para-phenylenediamines, used for dyeing keratin fibres, and in particular human hair, either in direct dyeing or in oxidation dyeing.

The nitro-para-phenylenediamines according to the invention correspond to the following formula (I)

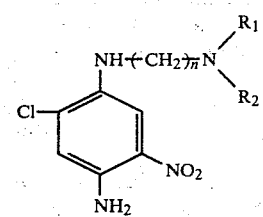

in which $R_1$ and $R_2$, which are identical or different, denote hydrogen, a lower (generally of 1 to 6 carbon atoms) alkyl group or a monohydroxylated or polyhydroxylated lower alkyl group and n is an integer from 2 to 4 inclusive, as well as the cosmetically acceptable salts of these compounds.

In the abovementioned formula, the alkyl radical preferably denotes a radical having from 1 to 4 carbon atoms.

Amongst the groups which are more particularly preferred, there may be mentioned, for the groups $R_1$ and $R_2$, hydrogen, methyl, ethyl and β-hydroxyethyl.

The salts can be, in particular, the hydrochlorides, hydrobromides or sulphates.

This invention also provides a process for the preparation of the compounds of the formula (I), by the direct reaction of a halogen derivative of the formula II:

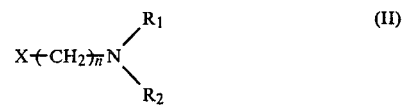

with 2-chloro-4-amino-5-nitroaniline.

The direct condensation can be carried out either in water or in a solvent, such as dioxane, in the presence of calcium carbonate.

In the case where $R_1$ and $R_2$ are different from hydrogen and denote alkyl or substituted alkyl, another process consists in reacting the derivative of the formula (II) with an alkali metal salt or alkaline earth metal salt of 2-chloro-4-amino-5-nitro-N-arylsulphonylaniline, and in hydrolysing the substituted arylsulphonamides thus obtained.

The condensation of the derivative (II) is advantageously carried out in dimethylformamide at 60° to 100° C. The hydrolysis of the substituted derivatives can be carried out either with concentrated hydrochloric acid under reflux or with concentrated sulphuric acid at about 0° C.

The compositions according to the invention are characterised in that they contain at least one compound corresponding to the formula (I), in a cosmetically acceptable solvent medium; they can be used for the direct dyeing of keratin fibres or in the oxidation dyeing of these fibres in which case these compounds of the formula (I) provide a complementary sheen for the basic coloration obtained by oxidising development of one or more oxidation dyestuff precursors.

These compositions generally contain the compounds according to the invention in an amount from 0.001 to 5% by weight, and preferably 0.01 to 3% by weight, relative to the total weight of the dyeing composition.

They can contain one or more anionic, cationic, non-ionic or amphoteric surface-active agents or mixtures thereof, and preferably cationic and/or non-ionic surface-active agents. These surface-active products are suitably present in the compositions of the invention in an amount from 0.5 to 55% by weight, and preferably 2 to 40% by weight, relative to the total weight of the composition.

In cosmetic application, the cosmetic vehicle generally consists of water, but it is also possible to add organic solvents to the compositions in order to solubilise compounds which would not otherwise be sufficiently soluble in water. Amongst these solvents, there may be mentioned lower alkanols, such as ethanol and isopropanol, polyols, such as glycerol, glycols or glycol ethers, such as 2-butoxyethanol, ethylene glycol, ethylene glycol monoethyl ether, propylene glycol, and diethylene glycol monoethyl ether and monomethyl ether, and analogous products and mixtures thereof. These solvents are preferably present in an amount from 1 to 75% by weight, and in particular from 5 to 50% by weight, relative to the total weight of the composition.

The compositions can be thickened, preferably with sodium alginate, gum arabic, a cellulose derivative, such as methylcellulose, hydroxyethylcellulose, hydroxypropylmethylcellulose or carboxymethylcellulose, or the various polymers serving as thickeners, such as acrylic acid derivatives. It is also possible to use inorganic thickeners, such as bentonite. These thickeners are preferably present in proportions of 0.5 to 10% by weight, and in particular 0.5 to 3% by weight, relative to the total weight of the composition.

The compositions according to the invention can also contain various adjuvants normally used in hair-dyeing compositions, and, in particular, penetrating agents, sequestering agents, film-forming agents, buffers, perfumes, alkalising agents and acidifying agents.

The composition can be presented in various forms, such as a liquid, a cream, a gel or any other form suitable for dyeing the hair. They can also be packaged in aerosol flasks, in the presence of a propellant.

The pH of these dyeing compositions is suitably 3 to 11.5 and preferably 5 to 11.5. It can be adjusted to the desired value with the aim of an alkalising agent, such as ammonia, sodium carbonate, potassium carbonate or ammonium carbonate, sodium hydroxide or potassium hydroxide, an alkanolamine, such as mono-, di- or triethanolamine, 2-amino-2-methylpropanol or 2-amino-2-methylpropane-1,3-diol, or an alkylamine, such as ethylamine, diethylamine or triethylamine, or with the aid of an acidifying agent, such as phosphoric, hydrochloric, tartaric, acetic, lactic or citric acid.

If the compositions are intended for use in a process for direct dyeing of the hair, they can contain, in addition to the compounds according to the invention, other direct dyestuffs, such as azo dyestuffs, anthraquinone dyestuffs, such as tetraaminoanthraquinone, aminoquinones, and nitro dyestuffs of the benzene series which are different from the compounds of the formula (I), and, more particularly, the following compounds: 2-methyl-6-nitroaniline, 3-nitro-4-aminophenol, 3-nitro-4-N-($\beta$-hydroxyethyl)-aminophenol, 3-nitro-4-amino-6-methylphenol, 3-amino-4-nitrophenol, 2-amino-3-nitrophenol, 3-nitro-6-N-($\beta$-hydroxyethyl)-aminoanisole, 3-N-($\beta$,$\gamma$-dihydroxypropyl)-amino-4-nitroanisole, (3-N-methylamino-4-nitro)-phenoxyethanol, (3-N-methylamino-4-nitro)-phenyl $\beta$,$\gamma$-dihydroxypropyl ether, N,N'-di-($\beta$-hydroxyethyl)-nitro-para-phenylenediamine and 3-nitro-4-N'-methylamino-N,N-(di-$\beta$-hydroxyethyl)-aniline. The concentrations of these direct dyestuffs other than the dyestuffs of the formula (I) is suitably from 0.001 to 5% by weight, relative to the total weight of the composition.

These compositions are applied to the keratin fibres for, say, 5 to 70 minutes, and the fibres are then rinsed, optionally washed and rinsed again, and dried.

These compositions can also be used in the form of a hair-setting lotion intended for simultaneously providing the hair with a slight coloration and improving the hold of the set. In this case, they are suitably presented in the form of aqueous, alcoholic or aqueous-alcoholic solutions containing at least one cosmetic resin, and they are applied to damp hair, washed and rinsed beforehand, which is optionally wound onto rollers and then dried.

The cosmetic resins used in the setting lotions can be, in particular, polyvinylpyrrolidone, crotonic acid/vinyl acetate copolymers, vinylpyrrolidone/vinyl acetate copolymers, monoesters of maleic anhydride/butyl vinyl ether copolymers, monoesters of maleic anhydride/methyl vinyl ether copolymers, as well as any other cationic, anionic, non-ionic or amphoteric polymer normally used in this type of composition. These cosmetic resins are suitably present in the compositions of the invention in an amount from 1 to 3% by weight, and preferably 1 to 2% by weight, based on the total weight of the composition.

If the compositions constitute oxidation dyes, the compounds of the formula (I) according to the invention are essentially used to provide the final dyeing with a sheen.

These compositions then contain oxidation dyestuff precursors, in association with at least one nitro dyestuff of the formula (I).

They can contain, for example, para-phenylenediamines, such as: para-phenylenediamine, para-toluylenediamine, 2,6-dimethyl-para-phenylenediamine, 2,6-dimethyl-3-methoxy-para-phenylenediamine, N-($\beta$-methoxyethyl)-para-phenylenediamine, 4-N,N-di($\beta$-hydroxyethyl)aminoaniline, 4-(N-ethyl-N-carbamylmethyl)-aminoaniline or a salt thereof.

They can also contain para-aminophenols, for example: para-aminophenol, N-methyl-para-aminophenol, 2-chloro-4-aminophenol, 3-chloro-4-aminophenol, 2-methyl-4-aminophenol or a salt thereof.

They can also contain heterocyclic derivatives, for example: 2,5-diaminopyridine and 7-aminobenzomorpholine.

The compositions according to the invention can contain, in association with the oxidation dyestuff precursors, couplers which are well known in the state of the art.

As couplers, there may be mentioned in particular: meta-diphenols, such as resorcinol and 2-methylresorcinol, meta-aminophenols, such as: meta-aminophenol, 2-methyl-5-aminophenol, 2-methyl-5-N-($\beta$-hydroxyethyl)-aminophenol, 6-hydroxybenzomorpholine and their salts, meta-phenylenediamines, such as: 2,4-diaminophenoxyethanol, 6-aminobenzomorpholine, [2-N-($\beta$-hydroxyethyl)-amino-4-amino]phenoxyethanol, 2,4-diaminophenyl $\beta$,$\gamma$-dihydroxypropyl ether and their salts, and meta-acylaminophenols, meta-ureidophenols and meta-carbalkoxyaminophenols, such as: 2-methyl-5-acetylaminophenol, 2-methyl-5-ureidophenol and 2-methyl-5-carbethoxyaminophenol.

Other couplers which can be used in the compositions of the invention, include: $\alpha$-naphthol, couplers possessing an active methylene group, such as diketone compounds and pyrazolones, and heterocyclic couplers, such as 2,4-diaminopyridine, and also their salts.

These compositions generally contain, in addition to the oxidation dyestuff precursors, reducing agents, such as sodium sulphite, thioglycolic acid, thiolactic acid, sodium bisulphite, ascorbic acid and hydroquinone. These reducing agents are suitably present in an amount from 0.05 to 1.5% by weight, relative to the total weight of the composition. The oxidation dyestuff precursors are suitably used in the compositions of the invention in concentrations from 0.001 to 5% by weight, and preferably from 0.03 to 2% by weight, based on the total weight of the composition. The couplers are also suitably present in concentrations of 0.001 to 5% by weight and preferably 0.015 to 2% by weight.

Their pH is preferably from 7 to 11.5 and can be adjusted with the aid of an alkalising agent defined above.

The process for dyeing keratin fibres, in particular human hair, using development with an oxidising agent consists in applying, to the hair, the dyeing composition comprising both a dyestuff according to the invention and one or more dyestuff precursors, and in developing the coloration with the aid of an oxidising agent which is either present in the dyeing composition or is applied to the hair in a second stage.

The oxidising agent is preferably hydrogen peroxide, urea peroxide or a per-salt. A solution of hydrogen peroxide of 20 volumes strength is used in particular.

Once the composition has been applied to the keratin fibres, with the oxidising agent, they are left for, say, 10 to 50 minutes, preferably 15 to 30 minutes, after which the keratin fibres are rinsed, optionally shampooed and rinsed again, and dried.

The following Examples further illustrate the present invention.

PREPARATION EXAMPLE 1

Preparation of 2-chloro-4-amino-5-nitro-N-β-aminoethylaniline and also the hydrobromide and the hydrochloride corresponding to this compound

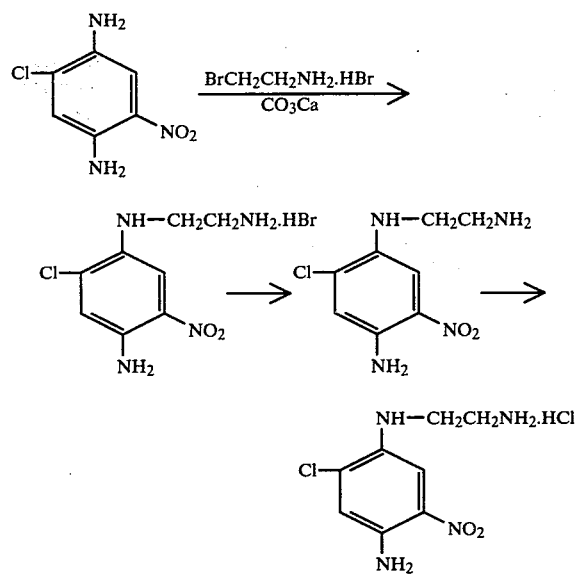

0.1 mol (18.7 g) of 2-chloro-4-amino-5-nitroaniline and 0.1 mol (10 g) of calcium carbonate are introduced into 50 ml of dioxane, and this mixture is then heated to about 90° C., with stirring. 0.15 mol (30.73 g) of bromoethylamine hydrobromide is added thereto in the course of 30 minutes. When the addition has ended, the heating is maintained for 4 hours at 90° C. The hot reaction medium is filtered. On cooling of the filtrate, the expected product crystallises in the form of the monohydrobromide.

The hydrobromide is filtered off, washed with a small amount of cold water and dried. The hydrobromide obtained above is added to 100 ml of water, and the solution is then rendered alkaline to pH 11 with the aid of a 10N sodium hydroxide solution, with stirring. The 2-chloro-4-amino-5-nitro-N-β-aminoethylaniline thus freed from its hydrobromide is filtered off. After washing with water, drying and recrystallisation from ethyl acetate, the product melts at 133° C.

6.4 g of 2-chloro-4-amino-5-nitro-N-β-aminoethylaniline are dissolved in 100 ml of absolute alcohol. 10 ml of a saturated solution of hydrogen chloride in absolute alcohol are added. The product precipitates in the form of the hydrochloride. This hydrochloride is filtered off and recrystallised with the aid of a 50/50 aqueous-alcoholic solution. This yields the monohydrochloride of 2-chloro-4-amino-5-nitro-N-β-aminoethylaniline, which, once dry, melts at about 265° C. with decomposition.

| Analysis | Calculated for $C_8H_{11}ClN_4O_2 \cdot HCl$ | Found |
|---|---|---|
| C % | 35.97 | 36.00 |
| H % | 4.53 | 4.56 |
| N % | 20.98 | 21.04 |
| O % | 11.98 | 12.09 |
| Cl % | 26.55 | 26.46 |

PREPARATION EXAMPLE 2

Preparation of 2-chloro-4-amino-5-nitro-N-β-diethylaminoethylaniline

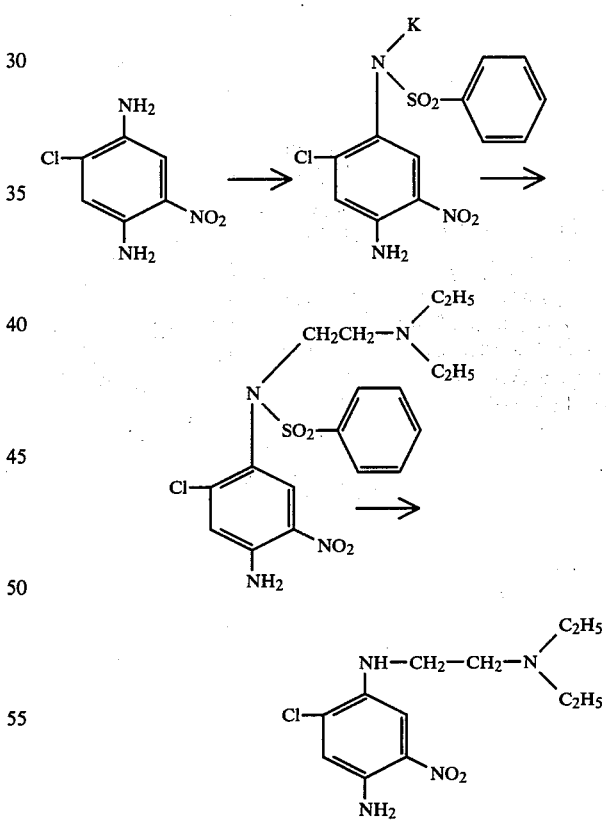

1st step

Preparation of the potassium salt of 3-chloro-4-N-benzenesulphonylamino-6-nitroaniline 0.16 mol (30 g) of 2-chloro-5-nitro-paraphenylenediamine is dissolved in 90 ml of pyridine. 0.168 mol (29.6 g) of benzenesulphonyl chloride is added gradually to this pyridine solution, at about 45°

C., with stirring, and the reaction medium is then kept at 40° C. for 1 hour. The pyridine solution is then poured into 850 ml of iced 1.5N hydrochloric acid solution. The expected product precipitates in the crystalline form. It is filtered off, washed with water and recrystallised from acetic acid. After drying, it melts at 176° C.

0.134 mol (44 g) of the benzenesulphonamide obtained above is introduced into 270 ml of absolute alcohol. 68 ml of alcohol containing 0.17 mol (9.52 g) of potassium hydroxide are added to this suspension, with stirring. This yields a homogeneous red solution, but the expected potassium salt precipitates very rapidly. It is filtered off, washed with a small amount of alcohol and dried in vacuo.

2nd step

Preparation of 3-chloro-4-(N-diethylaminoethyl-N-benzenesulphonyl)-amino-6-nitroaniline 0.16 mol (58.7 g) of the potassium salt of 3-chloro-4-N-benzenesulphonylamino-6-nitroaniline is introduced into 150 ml of dimethylformamide at about 90° C. 0.18 mol (24.4 g) of diethylaminoethyl chloride is added gradually, with stirring. When the addition has ended, the reaction medium is kept at 80° C. for 2 hours and then poured into 500 ml of iced water. The expected product precipitates in the form of a gum, which crystallises rapidly. The crystalline product is filtered off, washed with water, dried in vacuo and recrystallised twice from ethyl acetate and then once from alcohol. After drying, it melts at 145° C.

3rd step

Preparation of 2-chloro-4-amino-5-nitro-N-$\beta$-diethylaminoethylaniline 0.047 mol (20 g) of the substituted benzenesulphonamide obtained in the previous step is introduced gradually into 80 ml of 96% strength sulphuric acid at between 8° and 12° C., with stirring. The reaction medium is kept at this temperature for 6 hours, with stirring. The dissolution of the starting material is then complete. The sulphuric acid solution is then poured into 500 g of crushed ice. The mixture is neutralised with 20% strength ammonia solution. The expected product precipitates in the form of a gum, which crystallises rapidly. The crystalline product is filtered off, washed with water, dried and recrystallised from cyclohexane.

After drying, it melts at 69° C.

| Analysis | Calculated for $C_{12}H_{19}N_4O_2Cl$ | Found |
| --- | --- | --- |
| C % | 50.26 | 50.28 |
| H % | 6.68 | 6.66 |
| N % | 19.54 | 19.53 |
| O % | 11.16 | 11.22 |
| Cl % | 12.30 | 12.46 |

EXAMPLE 1

The following dyeing composition is prepared:
2-Chloro-4-amino-5-nitro-N-$\beta$-aminoethylaniline hydrochloride—0.25 g
2-Butoxyethanol—10 g
Diethanolamides of copra fatty acids—2.2 g
Lauric acid—0.8 g
Ethylene glycol monoethyl ether—2 g
Triethanolamine containing 20% of active ingredient—5 g
Water q.s.p.—100 g
pH 8.9

When applied for 30 minutes at 30° C. to hair which has been bleached white, this mixture imparts to the hair, after rinsing and shampooing, a red coloration and more precisely a coloration of 7.5 R 4.5/10 on the Munsell scale.

EXAMPLE 2

The following dyeing composition is prepared:
2-Chloro-4-amino-5-nitro-N-$\beta$-aminoethylaniline hydrochloride—0.09 g
3-Nitro-4-N-($\beta$-aminoethyl)-amino-N',N'-dihydroxyethylaniline dihydrochloride—0.155 g
(3-N-Methylamino-4-nitro)-phenyl $\beta,\gamma$-dihydroxypropyl ether—0.23 g
Propylene glycol—5 g
96° strength alcohol—5 g
Cemulsol NP$_4$—12 g
Cemulsol NP$_9$—15 g
Oleyl alcohol oxyethyleneated with 2 mols of ethylene oxide—1.5 g
Oleyl alcohol oxyethyleneated with 4 mols of ethylene oxide—1.5 g
20% strength monoethanolamine solution—2 g
Water q.s.p.—100 g
pH 10.2

When applied for 25 minutes at 30° C. to hair which has been bleached straw yellow, this mixture imparts to the hair, after rinsing and shampooing, a coppery medium chestnut coloration.

EXAMPLE 3

The following dyeing composition is prepared:
2-Chloro-4-amino-5-nitro-N-$\beta$-aminoethylaniline hydrochloride—0.3 g
3-Nitro-4-N-methylamino-N',N'-dihydroxyethylaniline—0.15 g
3-Nitro-4-aminophenol—0.1 g
Propylene glycol—8 g
96° strength ethanol—2 g
Carbopol 934—2 g
Pure triethanolamine—5 g
Water q.s.p.—100 g
pH 7.8

When applied to 90% naturally white hair for 30 minutes at 28° C., this mixture imparts to the hair, after rinsing and shampooing, a russet coloration.

EXAMPLE 4

The following dyeing composition is prepared:
2-Chloro-4-amino-5-nitro-N-$\beta$-aminoethylaniline hydrochloride—1 g
2-Butoxyethanol—10 g
Alfol C$_{16/18}$—8 g
Lanette wax—0.5 g
Cemulsol B—1 g
Oleic diethanolamide—1.5 g
22° B strength ammonia solution—5 g
Water q.s.p.—100 g
pH 10.2

When applied to 90% naturally white hair for 30 minutes at 30° C., this mixture imparts to the hair, after rinsing and shampooing, a strong red coloration of 6 R ⅜ on the Munsell scale.

EXAMPLE 5

The following dyeing composition is prepared:
2-Chloro-4-amino-5-nitro-N-β-aminoethylaniline hydrochloride—0.1 g
Tetraaminoanthraquinone—0.25 g
2-Methyl-6-nitroaniline—0.07 g
Cemulsol NP$_4$—12 g
Cemulsol NP$_9$—15 g
Oleyl alcohol oxyethyleneated with 2 mols of ethylene oxide—1.5 g
Oleyl alcohol oxyethyleneated with 4 mols of ethylene oxide—1.5 g
20% strength monoethanolamine solution—5 g
Water q.s.p.—100 g
pH 10.8

When applied to bleached hair for 30 minutes at 28° C., this mixture imparts to the hair, after rinsing and shampooing, a golden light blond coloration with a pink sheen.

EXAMPLE 6

The following dyeing composition is prepared:
2-Chloro-4-amino-5-nitro-N-β-aminoethylaniline hydrochloride—0.08 g
4-Nitro-N,N'-β-hydroxyethyl-ortho-phenylenediamine—0.3 g
2-N-(β-Hydroxyethyl)-amino-5-[4-di-(β-hydroxyethyl)-aminoanilino]-1,4-benzoquinone 0.2 g
3-Nitro-4-N-methylamino-N'-β-aminoethylaniline dihydrobromide—0.215 g
2-Butoxyethanol—10 g
Carboxymethylcellulose—2 g
Ammonium lauryl-sulphate—5 g
4% strength ammonia solution—3 g
Water q.s.p.—100 g
pH 9.2

When applied for 25 minutes at 30° C. to hair which has been bleached straw yellow, this mixture imparts to the hair, after rinsing and shampooing, a copper-red chestnut coloration.

EXAMPLE 7

The following dyeing composition is prepared:
2-Chloro-4-amino-5-nitro-N-β-aminoethylaniline hydrochloride—0.15 g
2-N-(β-Hydroxyethyl)-amino-5-nitrophenol—0.38 g
Resorcinol—0.08 g
meta-Aminophenol—0.05 g
ortho-Aminophenol—0.05 g
para-Phenylenediamine—0.15 g
2,4-Diaminophenoxyethanol dihydrochloride—0.04 g
Cemulsol NP$_4$—12 g
Cemulsol NP$_9$—15 g
Oleyl alcohol containing 2 mols of ethylene oxide—1.5 g
Oleyl alcohol containing 4 mols of ethylene oxide—1.5 g
Propylene glycol—6 g
Trilon B—0.12 g
Thioglycolic acid—0.6 g
22° B strength ammonia solution—11 g
Water q.s.p.—100 g
pH 10.2

An equal weight of hydrogen peroxide of 20 volumes strength is added at the time of use.

When applied for 30 minutes at 28° C. to hair which has been bleached white, this mixture imparts to the hair, after rinsing and shampooing, a red chestnut coloration.

EXAMPLE 8

The following dyeing composition is prepared:
2-Chloro-4-amino-5-nitro-N-β-diethylaminoethylaniline—1.5 g
2-Butoxyethanol—10 g
Hydroxyethylcellulose sold under the name Cellosize WP 03 by Union Carbide—2 g
Cetyldimethylhydroxyethylammonium chloride—2 g
Water q.s.p.—100 g
pH 8.5

When applied to bleached hair for 20 minutes at 30° C., this mixture imparts to the hair, after rinsing and shampooing, a red coloration of 7.5 R 4.5/11 on the Munsell scale.

EXAMPLE 9

The following dyeing composition is prepared:
2-Chloro-4-amino-5-nitro-N-β-aminoethylaniline hydrochloride—0.4 g
2-Methyl-6-nitroaniline—0.315 g
3-Nitro-4-N'-methylamino-N-β-aminoethylaniline dihydrobromide—0.24 g
2-Butoxyethanol—10 g
Hydroxyethylcellulose sold under the name Cellosize WP 03 by Union Carbide—2 g
Cetyldimethylhydroxyethylammonium chloride—2 g
22° B strength ammonia solution—0.8 g
Water q.s.p.—100 g
pH 9

When applied to 90% naturally white hair for 30 minutes at 28° C., this mixture imparts to the hair, after rinsing and shampooing, a mahogany coloration.

The various tradenames used in the foregoing Examples are explained in greater detail below:

CARBOPOL 934: Acrylic acid polymer with a molecular weight of 2 to 3 million, sold by Goodrich Chemical Company.

CEMULSOL NP$_4$: Nonylphenol oxyethyleneated with 4 mols of ethylene oxide, sold by Rhône Poulenc.

CEMULSOL NP$_9$: Nonylphenol oxyethyleneated with 9 mols of ethylene oxide, sold by Rhône Poulenc.

ALFOL C$_{16/18}$: Cetyl/stearyl alcohol sold by (50/50): Condéa.

Lanette wax E: Partially sulphated cetyl/stearyl alcohol sold by Henkel.

CEMULSOL B: Oxyethyleneated castor oil sold by Rhône Poulenc.

TRILON B: Sodium salt of ethylenediaminetetraacetic acid.

We claim:

1. A nitro-para-phenylenediamine derivative which corresponds to the formula (I):

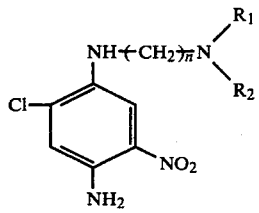

in which $R_1$ and $R_2$, which are identical or different, denote hydrogen, a lower alkyl group or a monohydroxylated or polyhydroxylated alkyl group and n is an integer from 2 to 4 inclusive, or a cosmetically acceptable salt thereof.

2. A derivative according to claim 1 in which the alkyl group denotes a group having 1 to 4 carbon atoms.

3. A derivative according to claim 1 or 2 in which $R_1$ and $R_2$ denote hydrogen or an ethyl group.

4. A derivative according to claim 1 which is 2-chloro-4-amino-5-nitro-N-$\beta$-aminoethyl aniline or a cosmetically acceptable salt thereof.

5. A derivative according to claim 1 which is 2-chloro-4-amino-5-nitro-N-$\beta$-diethylaminoethyl aniline or a cosmetically acceptable salt thereof.

6. A composition suitable for dyeing keratin fibres which comprises a diluent or carrier and at least one derivative as defined in claim 1 in an amount effective for dyeing hair.

7. A composition according to claim 6 for dyeing human hair which comprises a cosmetically acceptable medium and at least one said derivative in an amount from 0.001 to 5% by weight.

8. A composition according to claim 6 or 7, which comprises at least one of water, a lower alkanol or a polyol, glycol or glycol ether, or a mixture thereof.

9. A composition according to claim 6 or 7 which also comprises at least one of a surface-active agent, thickener, penetrating agent, sequestering agent, film-forming agent, buffer, perfume or alkalising or acidifying agent.

10. A composition according to claim 6 for use in the direct dyeing of the hair, which also comprises at least one other direct dyestuff which is an azo, anthraquinone, aminoquinone, or nitro benzene dyestuff.

11. A composition according to claim 6 which is in the form of an aqueous, alcoholic or aqueous-alcoholic solution containing at least one cosmetic resin.

12. A composition according to claim 10 or 11 which has a pH of 3 to 11.5.

13. A composition according to claim 10 or 11 which has a pH of 5 to 11.5.

14. A composition according to claim 6 for use in oxidation dyeing, which also comprises at least one oxidation dyestuff precursor.

15. A composition according to claim 14 which has a pH of 7 to 11.5 and contains a reducing agent.

16. Process for dyeing keratin fibres, which comprises applying thereto a composition as defined in claim 6, in an amount effective to dye hair, leaving it on the fibres for 5 to 70 minutes and then rinsing, optionally washing and rinsing again, the fibres and then drying them.

17. Process for dyeing keratin fibres which comprises applying a composition as defined in claim 11, in an amount effective to dye hair, to washed and rinsed fibres and drying them.

18. Process for dyeing keratin fibres, which comprises applying thereto a composition as defined in claim 14, in an amount effective to dye hair, to which an oxidising agent has optionally been added, leaving it on the fibres for 10 to 50 minutes and rinsing, optionally shampooing and rinsing the fibres again, and drying them.

19. Process for the preparation of a derivative as defined in claim 1 which comprises condensing a halogen derivative of the formula

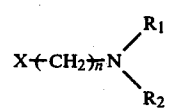

with 2-chloro-4-amino-5-nitroaniline where X is halogen and n is an integer of 2 to 4 inclusive.

20. Process for the preparation of a derivative as defined in claim 1 in which $R_1$ and $R_2$ are different from hydrogen, which comprises reacting a halogen derivative of the formula

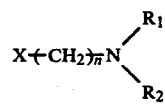

where X is halogen and n is an integer of 2 to 4, with an alkali metal, or alkaline earth metal salt of 2-chloro-4-amino-5-nitro-N-arylsulphonyl-aniline, and hydrolysing the substituted arylsulphonamide obtained.

* * * * *